United States Patent [19]

Evans

[11] Patent Number: 4,625,037

[45] Date of Patent: * Nov. 25, 1986

[54] METHOD FOR MAKING THIOETHER(BISPHTHALIMIDE)S

[75] Inventor: Thomas L. Evans, Clifton Park, N.Y.

[73] Assignee: General Electric Company, Schenectady, N.Y.

[*] Notice: The portion of the term of this patent subsequent to Feb. 12, 2002 has been disclaimed.

[21] Appl. No.: 576,224

[22] Filed: Feb. 2, 1984

[51] Int. Cl.$^4$ .............................................. C07D 209/48
[52] U.S. Cl. ...................................... 548/461; 549/241
[58] Field of Search .......................... 548/461; 549/241

[56] References Cited

U.S. PATENT DOCUMENTS

| | | | |
|---|---|---|---|
| 3,989,712 | 11/1976 | Williams, III | 548/461 |
| 4,054,584 | 10/1977 | Williams, III | 260/346.3 |
| 4,102,905 | 7/1978 | Williams, III et al. | 260/346.3 |
| 4,273,712 | 6/1981 | Williams, III | 260/326 N |
| 4,476,309 | 10/1984 | Verbicky, Jr. et al. | 548/461 |
| 4,499,285 | 2/1985 | Evans | 548/461 |

FOREIGN PATENT DOCUMENTS 55-122757  9/1980  Japan .................................. 548/461

*Primary Examiner*—George F. Lesmes
*Assistant Examiner*—S. A. Gibson
*Attorney, Agent, or Firm*—James Magee, Jr.; James C. Davis, Jr.

[57] ABSTRACT

A method is provided for making thioether-(bisphthalimide)s from an alkali metal hydrogen sulfide and an N-organo substituted halophthalimide or nitrophthalimide.

14 Claims, No Drawings

METHOD FOR MAKING THIOETHER(BISPHTHALIMIDE)S

The present invention concerns a new method for synthesizing thioether(bisphthalimide)s which are useful as intermediates for making polytherimides and also as plasticizers, fire retardants, and antioxidants in organic polymers. The invention concerns a method of converting N-substituted halophthalimides and nitrophthalimides to thioether(bisphthalimide)s utilizing an alkali metal hydrogen sulfide (herein referred to as "MHS") instead of an alkali metal sulfide ($M_2S$), where M is an alkali metal.

This method was discovered when attempts were made to prepare 4-N-methylphthalimide hydrogen sulfide. Surprisingly, the predominant product was 4,4'bis(N-methylphthalimide) from the reaction of a 1:1 mole ratio of sodium hydrogen sulfide to 4-chloro-N-methylphthalimide.

A method for synthesizing thioether(bisphthalimide)s from a reaction of an alkali metal sulfide and an N-substituted phthalimide has been accomplished and disclosed in U.S. Pat. No. 4,054,584. Utilizing MHS has advantages over the use of an alkali metal sulfide such as the ease of drying the hydrated form of MHS ($MHS.2H_2O$ where M is an alkali metal) as compared to drying the hydrated form of an alkali metal sulfide ($M_2S.9H_2O$, where M is an alkali metal prior to their use in synthesizing thioether(bisphthalimide)s. Also, the alkali metal hydrogen sulfides have improved solubility over alkali metal sulfides in organic solvents and therefore a smaller amount of solvent is required to facilitate reaction with phthalimides. This is particularly important since using dipolar aprotic solvents is costly. This improved solubility also permits higher yields to be obtained when using nonpolar solvents and a phase transfer catalyst than when utilizing alkali metal sulfides. This process has produced yields of thioether(bisphthalimide)s of over 40 percent with nonpolar solvents (see example 5). This is important when attempting to avoid the use of the costly dipolar aprotic solvents. In addition, a product of the reaction process is $H_2S$, which can be converted to the desired alkali metal hydrogen sulfide and recycled to the reaction process.

Included among the compounds provided by the method of the present invention are thioether(bisphthalimide)s of the formula,

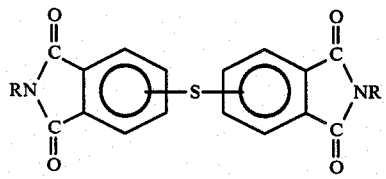

where R is a monovalent radical selected from $C_{(1-8)}$ alkyl and $C_{(6-20)}$ aromatic hydrocarbon radicals. These compounds may be converted by a known process to the corresponding anhydrides of the formula,

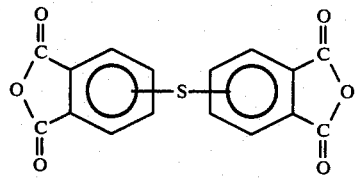

These thioether(bisphthalic anhydrides) of formula II may be employed as antioxidants in organic compounds, curing agents for epoxy resins, and as monomers in the formation of polyimides for high temperature use.

Not wishing to be bound by theory, it is believed that the thioether(bisphthalimide)s are produced in accordance with the following equations (see Example 7).

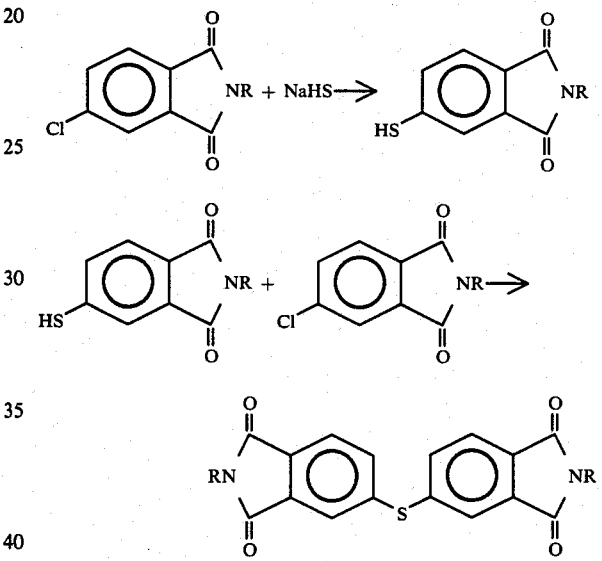

It is further believed that the alkali metal hydrogen sulfide acts as a base in removing hydrogen from the 4-n-methylphthalimide hydrogen sulfide initially formed producing an intermediate and $H_2S$. This intermediate is then converted to thioether(bisphthalimide)s by combining with the 4-chloro-N-methylphthalimide present in the reaction mixture.

The method of making the compounds of formula I provided by the present invention comprises the employment of a reaction of N-substituted nitrophthalimides or halophthalimides with an alkali metal hydrogen sulfide in (1) dipolar aprotic solvents or alternatively (2) in nonpolar solvents, preferably toluene, with a phase transfer catalyst present. The presence of a base such as triethyl amine, tributyl amine, etc., is preferred in both solvent systems to increase yields of thioether(bisphthalimide)s.

The alkali metal hydrogen sulfide (MHS) contains an alkali metal (M) such as sodium, potassium, lithium, etc. The alkali metal hydrogen sulfide may be in the hydrated form $MHS.2H_2O$ or in the anhydrous form. Sodium hydrogen sulfide (NaHS) is the preferred alkali metal sulfide used to produce the thioether(bisphthalimide)s.

The N-substituted phthalimides are of the formula

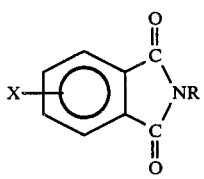

where X is either a nitro radical or a halo radical selected from fluoro, chloro, bromo and iodo; and R is a monovalent radical selected from $C_{(1-8)}$ alkyl radicals and $C_{(6-20)}$ aromatic radicals. Examples of radicals represented by R include, for example, methyl, ethyl, propyl, pentyl, octyl, isopropyl, etc.; and phenyl, tolyl, xylyl, naphthyl, chlorophenyl, bromotolyl, etc.

Some of the N-substituted halophthalimides and nitrophthalimides of formula III include, for example, 4-chloro-N-methylphthalimde, 4-chloro-N-phenylphthalimide, 4-nitro-N-methylphthalimide, etc. The preferred N-substituted phthalimides are 4-chloro-N-methylphthalimide and 4-nitro-methylphthalimide, which produde high yields of bis(thioetherphthalimide) when employed in a reaction having a molar ratio 4-chloro-N-methylphthalimide to the alkali metal hydrogen sulfide of 2:1.

The N-substituted phthalimide of formula III can be made by effecting reaction between substantially equal moles of organic amines, $RNH_2$ (where R is as previously defined), and a substituted phthalic anhydride of the formula,

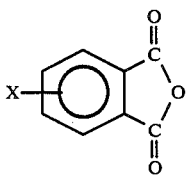

where x has been previously defined. Included by $RNH_2$ are organic amines such as aniline, toluidine, methylamine, ethylamine, etc.

The dipolar aprotic solvents which can be utilized include, for example, dimethylformamide, dimethylsulfoxide, dimethylacetamide, etc. Mixtures of such dipolar aprotic solvents with nonpolar solvents such as, for example, toluene, chlorobenzene, dichlorobenzene, etc., may also be employed. These nonpolar solvents, such as toluene, may be used without a dipolar aprotic solvent if a phosphonium salt phase transfer catalyst is present. The preferred catalysts are of the formula $P(R^1)_4{}^+Br$, where $R^1$ is a monovalent radical selected from the group consisting of $C_{(1-16)}$ alkyl radicals and $C_{(6-13)}$ aromatic carbocyclic radicals. These catalysts include, for example, tetrabutylphosphonium bromide, tetraphenylphosphonium bromide and tetracyclohexylphosphonium bromide and tetracyclohexylphosphonium bromide, etc. Tetrabutylphosphonium bromide is the preferred catalyst where a nonpolar solvent is employed, which is preferaly toluene. However, the use of dipolar aprotic solvents such as, for example, dimethylformamide and dimethylacetamide, produces higher yields than nonpolar solvents since the formation of thioether(bisphthalimide)s is faster in dipolar aprotic solvents.

To effect the reaction, the solution containing the alkali metal hydrogen sulfide and N-substituted phthalimide is maintained at a temperature in the range of 25° C. to 150° C., and preferably in the range of 70° C. to 150° C. for a period ranging from 2 to 24 hours or more, depending upon the temperature, solvent utilized, the degree of agitation, ingredients used, etc.

The thioether(bisphthalimide) product is recoverd from the resulting mixture by a precipitation process. Adding water to the reaction mixture is the preferred method to cause the product to precipitate from the solution. Cooling the reaction mixture is an alternative method. The precipitate is filtered, dried, and recrystallized from an organic solvent, such as a 90:10 weight mixture of dichlorobenzene and heptane respectively.

Some of the thioether(bisphthalimide)s that are produced are, for example, 3,3′-bis(N-methylphthalimide)sulfide, 4,4′-bis(N-methylphthalimide)sulfide; 3,3′-bis(N-phenylphthalimide)sulfide; 4,4′-bis(N-phenylphthalimide)sulfide; 3,3′-bis(n-butylphthalimide)sulfide; 4,4′-bis(N-butylphthalimide)sulfide; 3,4-bis(phenylphthalimide)sulfide, etc.

In order that those skilled in the art will be better able to practice the invention, the following examples are given by way of illustration and not by way of limitation.

EXAMPLE 1

To dry dimethylformamide (30 ml) were added 4-chloro-N-methylphthalimide (1.0 g, 0.0051 mol), sodium hydrogen sulfide (0.14 g, 0.0025 mol), biphenyl (0.20 g, 0.0013 mol) and triethylamine (0.4 ml, 0.0025 mol). The solution was heated to 145° C. for 12 hours. A sample of the reaction mixture was added to a dimethylformamide solution containing ethyl bromide and examined by high pressure liquid chromatography (HPLC) which indicated an 84% yield of 4,4′-bis(N-methylphthalimide)sulfide. The remaining reaction mixture was then added to water, the formed precipitate collected, dried, and recrystallized from a 90:10 weight mixture of o-dichlorobenzene and heptane. An isolated purified yield of 80% product (0.72 g) was obtained, which had a melting point of 239° C.

EXAMPLE 2

To dimethylformamide (30 ml) were added 4-chloro-N-methylphthalimide (0.498 g, 0.00255 mol), sodium hydrogen sulfide (0.15 g, 0.00268 mol), and biphenyl (0.42 g, 0.0054 mol). This reaction mixture was heated at 150° C. for 16 hours. A sample of the reaction mixture was removed, added to a dimethylformamide solution containing ethylbromide, and examined by HPLC. The HPLC test indicated a yield of 4,4′-bis(N-methylphthalimide)sulfide of 78.1% based on the quantity of 4-chloro-N-methylphthalimide used. The isolated yield was 65% (0.29 g).

EXAMPLE 3

To a reaction vessel containing dimethylacetamide (25 ml) were added 4-nitro-N-methylphthalimide (0.51 g, 0.00248 mol), biphenyl (0.21 g, 0.00139 mol), sodium hydrogen sulfide (0.14 g, 0.00125 mol) and triethylamine (0.2 ml, 0.0014 mol). The reaction was allowed to proceed at 70° C. for 24 hours. Samples of the reaction mixture were taken and examined by HPLC. A yield of 19.6% 4,4′-bis(N-methylphthalimide)sulfide was indicated. The isolated yield was 18% (0.08 g).

EXAMPLE 4

To a reaction vessel containing dimethylacetamide (25 ml) were added 4-nitro-N-methylphthalimide (0.50 g, 0.00243 mol), biphenyl (0.204 g, 0.00132 mol) and sodium hydrogen sulfide (0.14 g, 0.0025 mol). The reaction was allowed to proceed at 70° C. for 24 hours. Samples of the reaction mixture were taken and examined by HPLC methods. A yield of 16.3% 4,4'bis(N-methylphthalimide)sulfide was indicated. The isolated yield was 15% (0.035 g).

EXAMPLE 5

The following were added to a reaction vessel: 4-chloro-N-methylphthalimide (0.53 g, 0.0027 mol), sodium hydrogen sulfide (0.07 g, 0.00125 mol), triethylamine (0.2 ml, 0.0014 mol), tetrabutylphosphonium bromide (0.15 g, 0.00044 mol) and dry toluene (40 ml). The reaction was allowed to proceed at reflux (approximately 145° C.) for 18 hours. The reaction mixture was sampled and tested by HPLC, which indicated a yield of 4,4'-bis(N-methylphthalimide)sulfide of 48.2%. The isolated yield was 45% (0.21 g).

EXAMPLE 6

To a reaction vessel were added 4-nitro-N-methylphthalimide (0.51 g, 0.00248 mol), sodium hydrogen sulfide (0.07 g, 0.00125 mol), biphenyl (0.204 g, 0.00132 mol), triethylamine (0.2 ml, 0.0014 mol), tetrabutylphosphonium bromide (0.15 g, 0.00044 mol) and dry toluene (40 ml). The reaction mixture was allowed to proceed at reflux (approximately 145° C.) for 18 hours. The reaction mixture was sampled and tested by HPLC which indicated a yield of 4,4'-bis(N-methylphthalimide)sulfide of 10% (0.04 g).

EXAMPLE 7

This example was run to investigate the mechanism of the reaction between the alkali metal hydrogen sulfides and the N-substituted halophthalimides.

To dimethylformamide (30 ml) were added 4-chloro-N-methylphthalimide (0.0986 g, 0.0051 mol), sodium hydrogen sulfide (0.15 g, 0.00125 mol). The reaction mixture was heated to 120° C. for 18 hours. A sample of the reaction mixture was recovered and examined by HPLC. A 35% yield (0.31 g) of thioether(bis N-methylphthalimide) was obtained and a 50% yield (0.25 g) of the intermediate 4-N-methylphthalimide hydrogen sulfide was obtained.

It should be understood that the above examples reprsent only a limited number of bisimide sulfides of formula I which can be made in accordance with the practice of the invention.

What I claim as new and desire to secure by letters patent is:

1. A method of making thioether(bisphthalimide)s of the formula

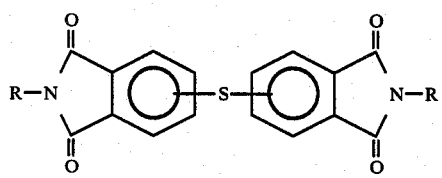

which comprises:

(a) heating at 25° C. to 150° C. an anhydrous mixture comprising N-substituted phthalimide of the formula,

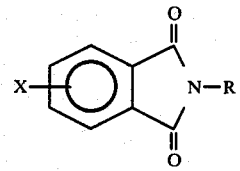

and an alkali metal hydrogen sulfide in the presence of an organic base selected from the group consisting of triethylamine and tributylamine and (1) a dipolar aprotic solvent or (2) a nonpolar organic solvent with an effective amount of a phosphonium salt phase transfer catalyst of the formula, $P(R')_4{}^+Br^-$, and (b) cooling said mixture to precipitate the thioether(bisphthalimide) product from said mixture:

wherein R is a monovalent radical selected from the group consisting of $C_{(1-8)}$ alkyl radicals and $C_{(6-20)}$ aromatic radicals, R' is selected from a group consisting of $C_{(1-6)}$ alkyl radicals and $C_{(6-13)}$ aromatic carbocyclic radicals, M is an alkali metal and X is a nitro radical or a halogen radical.

2. A method in accordance with claim 1 where the thioether(bisphthalimide) product is precipitated by the addition of water.

3. A method in accordance with claim 1 where the alkali metal hydrogen sulfide is sodium hydrogen sulfide.

4. A method in accordance with claim 1 where the N-substituted phthalimide is 4-chloro-N-methylphthalimide.

5. A method in accordance with claim 1 where said substituted phthalimide is 4-nitro-N-methylphthalimide.

6. A method in accordance with claim 1 where said dipolar aprotic solvent utilized is selected from the group consisting of dimethylformamide and dimethylacetamide.

7. A method in accordance with claim 1 where said nonpolar solvent utilized is toluene.

8. A method in accordance with claim 1 where said phosphonium salt phase transfer catalyst is tetrabutylphosphonium bromide.

9. A method in accordance with claim 3 where the molar ratio of 4-chloro-N-methylphthalimide to the alkali metal hydrogen sulfide is 2:1.

10. A method in accordance with claim 1 where said mixture is heated to a temperature in the range of 70° C. to 150° C.

11. A method of making 4,4'-bis(N-methylphthalimide)sulfide having the formula

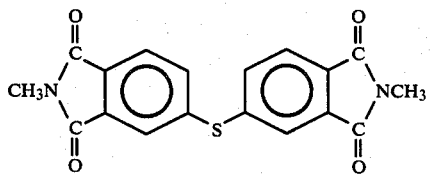

which comprises:

(a) heating at 25° C. to 150° C. an anhydrous mixture of 4-chloro-(N-methylphthalimide) and sodium hydrogen sulfide in the presence of dimethylformamide, a non-polar solvent selected from the group consisting of biphenyl and toluene and triethylamine and (b) precipitating 4,4'-bis(N-methylphthalimide sulfide).

12. A method of making 4,4-bis(N-methylphthalimide)sulfide having the formula,

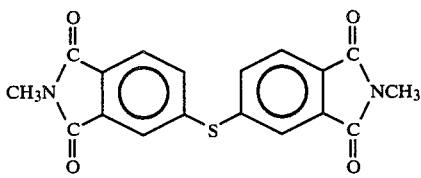

which comprises:
(a) heating at 25° C. to 150° C. an anhydrous mixture of 4-chloro(N-methylphthalimide) and sodium hydrogen sulfide in the presence of toluene, triethylamine and an effective amount of tetrabutylphosphonium bromide and (b) precipitating the 4,4'-bis(N-methylphthalimide)sulfide.

13. A method of making 4,4-bis(N-methylphthalimide)sulfide having the formula:

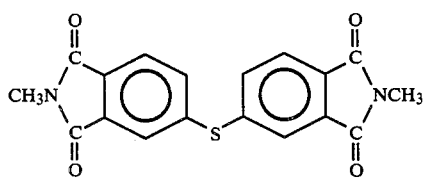

which comprises
(a) heating at 25° C. to 150° C. an anhydrous mixture of 4-Nitro-(N-methylphthalimide) and sodium hydrogen sulfide in the presence of dimethylformamide, a non-polar solvent selected from the group consisting of biphenyl and toluene and triethylamine;

(b) precipitating 4,4'-bis(N-methylphthalimide)sulfide.

14. A method of making thioether(bisphthalimide)s of the formula

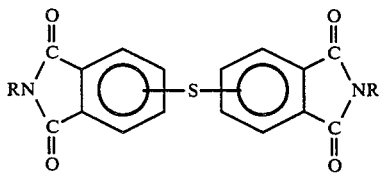

which comprises:
(a) heating at 25° C. to 150° C. an anhydrous mixture comprising N-substituted phthalimide of the formula,

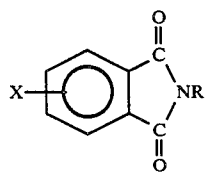

and an alkali metal hydrogen sulfide in the presence of a trialkylamine organic base and (1) a dipolar aprotic solvent or (2) a nonpolar organic solvent with an effective amount of a phosphonium salt phase transfer catalyst of the formula, $P(R')_4^+ Br^-$ and (b) cooling said mixture to precipitate the thioether(bisphthalimide) product from said mixture:
wherein R is a monovalent radical selected from the group consisting of $C_{(1-8)}$ alkyl radicals and $C_{(6-20)}$ aromatic radicals, R' is selected from a group consisting of $C_{(1-6)}$ alkyl radicals and $C_{(6-13)}$ aromatic carbocyclic radicals, M is an alkali metal and X is a nitro radical or a halogen radical.

* * * * *